(12) United States Patent
Smith

(10) Patent No.: US 6,800,301 B2
(45) Date of Patent: Oct. 5, 2004

(54) MULTI-PURPOSE SKIN BALM INCLUDING SKIN BALM FOR PSORIASIS

(75) Inventor: Sadie N. Smith, 5436 Winniespan Rd., Chattanooga, TN (US) 37416

(73) Assignee: Sadie N. Smith, Chattanooga, TN (US)

(*) Notice: Subject to any disclaimer, the term of this patent is extended or adjusted under 35 U.S.C. 154(b) by 220 days.

(21) Appl. No.: 09/829,272

(22) Filed: Apr. 9, 2001

(65) Prior Publication Data

US 2002/0146440 A1 Oct. 10, 2002

(51) Int. Cl.⁷ .................. A61K 33/00; A61K 7/00
(52) U.S. Cl. .............. 424/642; 424/401; 424/485; 574/782; 574/783; 574/861; 574/863; 574/864; 574/886; 574/887
(58) Field of Search ................... 424/145, 412, 424/401, 642, 485

(56) References Cited

U.S. PATENT DOCUMENTS

| | | | |
|---|---|---|---|
| 4,816,254 A | * 3/1989 | Moss | 424/144 |
| 4,847,071 A | * 7/1989 | Bissett et al. | 242/59 |
| 5,194,261 A | * 3/1993 | Pichierri | 424/401 |
| 5,496,296 A | 3/1996 | Holmberg | 604/336 |
| 6,036,966 A | * 3/2000 | Youssefyeh | 424/401 |

OTHER PUBLICATIONS

Physician Desk Reference, 1997, Medical Economics Company, Inc., Montvale, NJ, see entry for Mycostatin cream.*
Physicians' Desk Reference entry for Mycostatin cream.*

* cited by examiner

Primary Examiner—Shelley A. Dodson
(74) Attorney, Agent, or Firm—Sadie N. Smith

(57) ABSTRACT

The invention is a user friendly, multi-purpose ointment whose simple basic formula is a combination of karaya gum powder and a vehicle for dispersing, such as petrolatum. It can be designed to treat a variety of skin problems by adding some non-essential ingredients such as Vitamin A&D Ointment, Vitamin E cream or Lotion at the discretion of the user, in addition to various pharmaceuticals based on the cause of the problem such as an antibacterial, an antifungal, an anti-inflammatory agent, an antiviral, an anti-parasitic, or an enzymatic agent at the discretion of the health care provider or user.

9 Claims, No Drawings

MULTI-PURPOSE SKIN BALM INCLUDING SKIN BALM FOR PSORIASIS

CROSS-REFERENCE TO RELATED APPLICATIONS

Not applicable.

BACKGROUND

1. Field of Invention

This is a new use utility patent for a multi-purpose skin balm series produced by compounding already FDA approved drugs generally regarded as safe. Skin Balm For Psoriasis is the flagship product of this series.

2. Description of Prior Art

Treating damaged skin is a science and art that has always baffled healthcare professionals and individuals alike. The skin is the body's largest organ and a barrier and protector against harsh things in the environment. Injury and disease are always just around the corner waiting to destroy the skin's integrity.

Despite the numerous scientific advances related to skin care, there are ever-present problems confronting the skin. There are still vast numbers of persons who are suffering from chronic and debilitating skin conditions. Many have lost hope for relief or a cure that would improve their lifestyle. Consider a 1996 quote for the following populations of persons: psoriasis (7 million in the U.S. alone); stasis ulcers (6–7 million); burns (1.2 million); surgical wounds (45 million); diabetic ulcers (16 million). In addition there are those with eczema, Kaposis sarcoma, the skin lesions associated with AIDS, insect bites, pain swelling and inflammation of gout, simple cuts, scrapes, bruise, sprains, and many other conditions. People who are affected by these conditions long for quick and lasting relief.

Though there are several single agents on the market for damaged skin, the art of compounding is underused or is forgotten. Compounding allows you to consider all factors when dealing with skin that has been damaged. These factors include the actual loss of structure, bleeding, pain, swelling, infection, and decreased immunity that slows the skins ability to heal. Disability, lost income, and less that a quality life style must also be considered.

In addition, the scientific community frowns on any one product claiming to be effective against a wide variety of conditions of various causes and rightly so. One must ask, "What comprises this product?" "Is there one main ingredient or several present?" Many have forgotten the effect of synergism, where indeed, the whole is greater than the sum of its parts. Compounding allows for this phenomenon to be true. Many single use products address the cause of the damage that has occurred to the skin but offers no support to help the immune system produce the necessary factors to speed up the healing process compounding is in fast becoming a lost art.

Recent documentaries catering to new advances in medicine have shown cases of burned victims, those with psoriasis, and other chronic skin conditions who were given the "best care" known at this time, but the results were far inferior to what is being proposed by this invention. By inferior I mean that it took weeks and months of therapy and surgical procedures which amounted long term loss of productivity, and huge sums of money spent with less optimum cosmetic results.

Another such "best care" regimen consisted of bathing in the waters off the coast of Australia. One must deduct that such therapy too is inferior if so many people in that part of the world are still plagued by psoriasis without much hope for substantial improvement in their lifestyle and well-being. Time spent this mode of therapy also hinders productivity.

Two previous patents using karaya gum powder were reviewed. U.S. Pat. No. 5,496,296 lists its claim as protecting the skin surrounding a stoma such as a colostomy or ileostomy. U.S. Pat. No. 4,481,625,4 limits its claims for karaya gum powder to treating skin irritations-such as diaper rash and decubitus associated with diaper rash. This patent was listed with an E2 expired status for failure to pay maintenance fees.

SUMMARY

This invention is a graduated multi-purpose skin balm line of products of which SKIN BALM FOR PSORIASIS is the flagship product. The art of compounding makes this a superior line of products capable of helping the skin repair itself in a wide range of conditions in a shorter period of time, and with better cosmetic outcomes.

OBJECTS AND ADVANTAGES

Several objects and advantages of the present invention are:

(a) to provide a skin balm that can be used where ever there is damaged skin except the eyes.

(b) to provide a skin balm that is user friendly and easy to apply.

(c) to provide a skin balm that can be used by healthcare professionals as well as the individual.

(d) to provide a skin balm whose unique composition takes care of the many discomforts associated with damaged skin, such as, pain swelling, odor, and disfigurement.

(e) to provide a skin balm that helps remove dead tissue from wounds.

(f) to provide a skin balm that can act as a preventive measure for those at risk for skin problems, i.e. people with diabetes.

(g) to provide a skin balm reduces disability and loss of productivity.

(h) to provide a skin balm than can safely be used with other therapies.

(i) to provide a skin balm that can be used with prescriptive drugs such as autolytic or debrieding agents, and antiviral agents.

(j) to provide a skin balm whose basic formula has a long shelf life.

(k) to provide a skin balm whose basic formula is hypoallergenic.

(l) to provide a skin balm whose daily use allows for daily inspection to determine if you are on the right course or need to make a change in therapy (m) to provide a skin balm that has a cosmetic effect for burn victims.

(n) to provide a skin balm whose cost is affordable.

(o) to provide a skin balm that's capable of reducing healing time by 65–75%.

(p) to provide a skin balm that aids in the restoration of skin infested with parasites.

CONCLUSION, RAMIFICATIONS AND SCOPE

Accordingly, the reader will see that the Multi-Purpose Skin Series is indeed a versatile product whose usage can have a far reaching outcomes regarding major complications and chronic conditions associated with loss skin integrity and related disease states. The series allow the individual to take an active, positive, and meaningful role in his healthcare along side that of the healthcare provider.

In addition, the products can add meaning to an active lifestyle in terms of decreased time of disability, and cosmetic outcomes. They can also have a tremendous impact on the financial burdens that affect both the individual and healthcare industry as a whole.

It is hoped that through the patent process a way can be found to make people aware of what they can do for themselves in terms of healthcare. They will also be able to associate these products with a wide range of conditions that they had not previously associated with the basic ingredient, karaya gum powder.

DETAILED DESCRIPTION OF THE INVENTION

The multi-purpose skin balm series embodies a graduated number of over-the-counter ingredients compounded together. But two balms in the series contain an additional drug that requires a prescription.

A listing of the ingredients is as follows:
1. A white petrolatum—An inactive ingredient that function as a transport agent for the other ingredients.
2. A karaya gum powder—A hydro-colloid powder acting as the principle skin healing agent for controlling pain, swelling, odor, and scarring.
3. An aloe vera with vitamin E lotion—A cream that enhances the cosmetic effect of scarring control and provides a pleasant fragrance. It can be considered as a nonessential agent.
4. A vitamin D ointment/cream—A cream that helps with the healing process. It can be considered as a non-essential agent.
5. A low strength cortisone cream—A cream to treat the signs of allergic skin reactions such as redness and swelling and burning.
6. An anti-bacterial agent—An ointment/cream to heat bacterial infections of the skin.
7. An anti-fungal agent—A cream to treat fungal or yeast infections in skin lesions.
8. An anti-viral agent—A cream/ointment to treat wounds or lesions that are caused by viruses.
9. An autolytic agent—A cream/ointment that helps to debried and remove necrotic tissue.
10. An anti-parasitic agent—A gel that helps in the destruction of parasites and relieves the itching associated with their presence.

DESCRIPTION OF THE INVENTION

The following denotes the names and compositions of the multi-purpose line of products.
1. Basic Multi-Purpose Skin Balm—Hypoallergenic: White petrolatum and kayara gum powder.
2. Ultra Basic Multi-Purpose Skin Balm: White petrolatum, kayara gum powder, aloe vera with vitamin E lotion or cream.
3. Ultra I Multi-Purpose Skin Balm: White petrolatum, kayara gum powder, aloe with vitamin E lotion or cream, and an antibacterial ointment.
4. Ultra II Multi-Purpose Skin Balm: White petrolatum, kayara gum powder, aloe with vitamin E lotion or cream, and antibacterial ointment, and an anti-fungal ointment or cream.
5. Ultra III-1* Skin Balm For Psoriasis: White petrolatum, kayara gum powder, aloe with vitamin E lotion or cream, Vitamin D cream or ointment, an antibacterial, and an antifungal ointment or cream.
6. Ultra III-2* Skin Balm For Psoriasis: White petrolatum, karaya gum powder, aloe with Vitamin E lotion or cream, Vitamin D cream or ointment, an antibacterial ointment, an anti-fungal ointment or cream, and 1% or lesser over-the counter strength cortisone cream.
7. Ultra IV Multi-Purpose Anti-Viral Skin Balm: White petrolatum, karaya gum powder, Aloe with Vitamin E lotion or cream, Vitamin D cream or ointment, an antibacterial, and an antiviral ointment.
8. Ultra V Multi-Purpose Debriedment Skin Balm: White petrolatum, karaya gum powder, an antibacterial, and an enzymatic ointment
9. Ultra VI Multi-Purpose Anti-Parasitic Skin Balm: White petrolatum, karaya gum powder, an anti-parasitic agent.

PREPARATION OF THE INVENTION FOR USE

The product is prepared in a clean area using the following equipment:
The ingredients
Containers
Spatulas
Weigh boats
Scales
Gloves
mJars with caps and appropriate labels
A large or small quantity can be made as desired.
1. For the Basic Multi-Purpose HYPOALLERGENIC Skin Balm the desired quantity of white petrolatum is mixed with a quantity of karaya gum powder sufficient enough to be dispersed throughout the white petrolatum in its entirety. The ingredients are mixed until the compound reaches a smooth consistency and with a viscosity that permits a smooth adherence to the skin or tissue being treated. Apply to the affected areas twice a day. The product can be used on any areas except the eyes. The product is for external use only.
2. For the Ultra Basic Multi-Purpose Skin Balm the desired quantity of white petrolatum is mixed with a quantity of karaya gum powder sufficient enough to be dispersed throughout the white petrolatum in its entirety. The ingredients are mixed until the compound reaches a smooth consistency Next the aloe with vitamin E is added in an amount that can be dispersed throughout the compound but at the same time maintaining enough of the original viscosity to allow adherence to the skin or tissue. Apply to the affected areas twice a day. The product can be used in any areas except the eyes. The product is for external use only.
3. For the Ultra I Multi-Purpose Skin Balm, the desired quantity of white petrolatum is mixed with a quantity of karaya gum powder sufficient enough to be dispersed throughout the white petrolatum in its entirety. The mixture is blended to a smooth consistency. Next, the aloe vera with vitamin E lotion is added in an amount that is dispersed throughout the compound but at the same time maintaining enough of the original consistency to allow adherence to the skin Finally, add the antibacterial ointment at the rate of ½ ounce per 16 ounces of white petrolatum and mix the compound thoroughly. Apply to the affected areas twice daily. The product can be used on any tissues except the eyes. The product is for external use only.
4. For the Ultra II Multi-Purpose Skin Balm, the desired quantity of white petrolatum is mixed with a quantity of karaya gum powder sufficient enough to be dispersed throughout the white petrolatum in its entirety. The compound is blended it form a smooth consistency. Next, the aloe with vitamin E lotion is added in a quantity that can be dispersed throughout the compound but at the same time maintaining enough of the original viscosity to allow of adherence to the skin or tissue. Next, add the antibacterial ointment at a ratio of ½ ounce per 16 ounces of white petrolatum. Finally, add the antifungal cream at a rate of ½ ounce per 16 ounces of white petrolatum. Mix the compound thoroughly. Apply to affected areas twice a day. The product can be applied to all areas except the eyes. The product is for external use only.

5. For the Ultra III-1* Skin Balm For Psoriasis, the desired quantity of white petrolatum is mixed with a quantity of karaya gum powder sufficient enough to be dispersed throughout the white petrolatum in its entirety when blended to a smooth consistency Next, the aloe with vitamin E lotion or cream is added in an amount that can be dispersed throughout the compound but at the same time maintaining enough of the original consistency to allow for adherence to the skin and tissues. Next, add the vitamin D ointment or cream or ointment at a ratio of ½ ounce per 16 ounces of white petrolatum. Finally, add both the antibacterial ointment and the anti-fungal ointment at the rate of ½ ounce per 16 ounces of white petrolatum. Blend the compound until it has a smooth consistency. Apply the compound twice a day. It can be used on any part of the body except the eyes. It is for external use only.

6. For Ultra IIII-2* Skin Balm for Psoriasis, the desired quantity of white petrolatum is mixed with a quantity of karaya gum powder sufficient enough to be dispersed throughout the white petrolatum in its entirety when blended to a smooth consistency. Next, the aloe vera with vitamin E lotion or cream is added in an amount that can be dispersed throughout the compound but at the same time maintaining enough of the original consistency to allow for adherence to the skin tissue. Next, the vitamin D ointment or cream, the antibacterial ointment, the anti-fungal cream, and the low-strength cortisone cream each are added at the rate of ½ ounce per 16 ounces of white petrolatum. Blend the compound until it reaches a smooth consistency. Apply to the affected areas twice a day. It can be used on any body surface except the eyes. It is for external use only.

7. For the Ultra IV Multi-Purpose Anti-Viral Skin Balm, The desired quantity of white petrolatum is mixed with a quantity of karaya gum powder sufficient enough to be dispersed throughout the white petrolatum in its entirety. Next, the aloe vera with vitamin E lotion or cream is added in an amount that can be dispersed throughout the compound but at the same time maintaining enough of the compound's original consistency to allow for adherence to the skin tissue. Next the antibacterial, and the anti-viral ointment or cream each are added to the compound at the rate of ½ ounce per 16 ounces of white petrolatum. The product may be applied to any body surface except the eyes. Apply twice a day or as needed. For external use only.

8. For the Ultra V Multi-Purpose Debriedment Skin Balm, the desired quantity of white petrolatum is mixed with a quantity of karaya gum powder sufficient enough to be dispersed throughout the white petrolatum in its entirety. Next, the antibacterial ointment is added at the rate of ½ ounce per 16 ounces of white petrolatum. The compound is mixed to a smooth consistency. Next, the enzymatic ointment can be added to the compound at the rate of ½ ounce per 16 ounces of white petrolatum. An alternate method is that the enzymatic ointment can be kept separate and added directly to the affected areas and is followed by the application of the compound and covered with a moist dressing. Apply twice to any area except the eyes. For external use only.

9. For the Ultra VI Multi-Purpose Anti-Parasitic Skin Balm, the desired quantity of white petrolatum is mixed with a quantity of karaya gum powder sufficient enough to be dispersed throughout the white petrolatum in its entirety. Next, the antibacterial ointment is added at the rate of ½ ounce per 16 ounces of white petrolatum. The compound is mixed to a smooth consistency. Must supply own anti-parasitic agent and maintain separate from skin balm. The skin balm is applied to the body first. The antiparasitic agent is applied only to the lesions as directed on its container. For external use only.

What is claimed is:

1. A multi-purpose hypoallergenic skin balm consisting of karaya gum powder and a vehicle for dispersing, wherein the vehicle for dispensing is white petrolatum, whereby pain, swelling, odors, drainage, scarring, and healing time is reduced along with enhanced debriedment when applied to a variety of wounds or damaged skin, thus restoring lost skin integrity.

2. The multi-purpose, hypoallergenic skin balm of claim 1 further consisting of aloe vera and vitamin E lotion or cream.

3. The multi-purpose, hypoallergenic skin balm of claim 2 further consisting of an antibacterial ointment.

4. The multi-purpose, hypoallergenic skin balm of claim 3 furthering consisting of an anti-fungal ointment or cream.

5. The multi-purpose, hypoallergenic skin balm of claim 2 further consisting of Vitamin D cream or ointment, an antibacterial, and an anti-fungal ointment or cream.

6. The multi-purpose, hypoallergenic skin balm of claim 5 further consisting of 1% or less of an over-the-counter strength cortisone cream.

7. The multi-purpose, hypoallergenic skin balm of claim 2 further consisting of Vitamin D cream or ointment, an antibacterial agent and an antiviral ointment.

8. The multi-purpose, hypoallergenic skin balm of claim 1 further consisting of an antibacterial agent, and an enzymatic ointment.

9. The multi-purpose, hypoallergenic skin balm of claim 1 further consisting of an ant-parasitic agent.

* * * * *